(12) United States Patent
Seher et al.

(10) Patent No.: US 7,509,232 B2
(45) Date of Patent: Mar. 24, 2009

(54) SYSTEM FOR POINT OF CARE DIAGNOSIS AND/OR ANALYSIS

(75) Inventors: Jens-Peter Seher, Stuttgart (DE); Gerhard Pross, Weil im Schönbuch (DE); Christopher Sprague Boit, Wellesley (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 415 days.

(21) Appl. No.: 10/513,527

(22) PCT Filed: May 5, 2003

(86) PCT No.: PCT/IB03/01751

§ 371 (c)(1), (2), (4) Date: Nov. 4, 2004

(87) PCT Pub. No.: WO03/094712

PCT Pub. Date: Nov. 20, 2003

(65) Prior Publication Data

US 2005/0214929 A1 Sep. 29, 2005

(30) Foreign Application Priority Data

May 8, 2002 (EP) .................................. 02010426

(51) Int. Cl.
*G21C 17/00* (2006.01)
(52) U.S. Cl. ..................................................... 702/183
(58) Field of Classification Search .................. 702/19, 702/62, 68, 119, 122, 131, 183, 188, 189; 422/104; 600/484; 204/403.02
See application file for complete search history.

(56) References Cited

U.S. PATENT DOCUMENTS

| 4,416,596 | A | * | 11/1983 | Lichtenstein | 417/488 |
| 5,375,604 | A | * | 12/1994 | Kelly et al. | 600/484 |
| 6,074,616 | A | * | 6/2000 | Buechler et al. | 422/104 |
| 2002/0005707 | A1 | * | 1/2002 | Kerai et al. | 320/106 |
| 2004/0173456 | A1 | * | 9/2004 | Boos et al. | 204/403.02 |

OTHER PUBLICATIONS

Microsoft Press, Computer Dictionary Third Edition, pp. 300 and 438.*

* cited by examiner

*Primary Examiner*—Edward Raymond
*Assistant Examiner*—Mohamed Charioui

(57) ABSTRACT

A system (1) for point of care diagnosis and/or analysis of a body fluid of a patient, includes at least one cartridge (2), at least one handheld diagnosis and/or analysis device (3) and at least one data processing device (4). Each cartridge (2) comprises a sample receiving room (5) for receiving a sample of the body fluid to be diagnosed and/or analyzed, a diagnosing and/or analyzing arrangement (6) for measuring at least one physiological parameter of the sample, and a first interface (7) for connecting the cartridge (2) to the handheld device (3). Each handheld device (3) comprises one second interface (8) for connecting one of said cartridges (2) to the handheld device (3), a measurement arrangement (9) co-operating with the connected cartridge (2) for measuring the parameter and generating measurement data thereof, and one third interface (13) for connecting the handheld device (3) to the data processing device (4). Each data processing device (4) comprises one fourth interface (14) for connecting one of said handheld devices (3) to the data processing device (3), and a data processing unit (15) co-operating with the connected handheld device (3) for further processing the measurement data.

19 Claims, 3 Drawing Sheets

SYSTEM FOR POINT OF CARE DIAGNOSIS AND/OR ANALYSIS

The present invention relates to a system for point of care diagnosis and/or analysis of a body fluid of a patient. The invention also relates to a handheld device and a data processing device of this system.

For measuring physiological parameters, more or less complex systems and in sizes ranging from small handheld devices to room-filling installations are applied. Mainly dependent on size, cost and mobility, the measuring device can be physically brought to the patient or the patient, or a sample out of the patient has to be moved to a remote measuring device.

Some devices, such as patient monitors, are mainly installed close to the patient's bed, while other small patient monitoring devices, e.g. in combination with telemetry applications, might even be worn by the patient allowing great flexibility and comfort for the patient. Other devices, such as analyzers for tissue samples or body fluid samples, are mainly installed at the clinical laboratory side. Those samples have to be drawn from the patient, unambiguously labeled and sent to the clinical laboratory. After analysis, the results are sent back, or the data is input into data bases or other devices. It is clear, that such a procedure is time consuming, involves different people from the clinical staff and might be a source for errors or false results.

In the field of point of care blood analysis, blood samples can be taken from the patient and directly and immediately analyzed at the point of care mainly using cartridges. Those cartridges comprise a sample receiving room for receiving a sample of the blood to be analyzed. The cartridge includes an analyzing arrangement for measuring physiological parameters of the blood sample. The cartridge may be coupled to an analyzing device, comprising a measurement arrangement, which co-operates with the cartridge connected to the analyzing device. The measurement arrangement is provided for measuring the physiological parameters and generating measurement data thereof. The measurement data may then be simply output on an internal screen or internal printer of the analyzing device, and has to be manually input into patient's charts, patient monitors or data bases.

It is an object of the present invention to provide an improved diagnosis and/or analysis system allowing great flexibility and mobility to patients as well as to clinical staff.

The object is solved by the independent claims. Preferred embodiments are shown by the dependent claims.

According to the invention, a diagnosis and/or analysis system comprises one or more handheld diagnosis and/or analysis devices, each being adapted for measuring e.g. a physiological parameter or a set of physiological parameters of a patients body fluid sample. The diagnosis and/or analysis system further comprises one or more data processing devices for further processing data (e.g. of the physiological parameter) as measured by the handheld diagnosis and/or analysis device(s).

While each handheld device basically represents a standalone device for providing the measurement (e.g. of the physiological parameter), it can be stacked with other handheld devices and/or coupled to each one of the data processing devices in order to communicate the measured data and/or control data, which might then be further processed by the data processing device, e.g. to a further data processing unit. This data processing includes simple data transfer to another data processing unit. In case that the data processing device, like a monitor, printer or display, is unable to handle multi-patient data, the handheld device will be configured such way, that it performs measurements only if it is coupled to each one of the data processing devices.

Each handheld device can be coupled to a respective one of the data processing devices for data communication. The coupling between a respective one of the handheld devices and a respective one of the data processing devices will be maintained as long as the data communication is going on, or until the handheld device will be separated from the respective data processing device.

The system according to the invention on the one hand allows direct and immediate analyzing and measurement of body fluid samples at the point of care. On the other hand the system allows the use of one single data processing device together with several handheld devices. As handheld devices are cheaper than stationary data processing devices the costs of care services can be decreased.

In another embodiment at least one of said handheld devices comprises a memory or storage for unambiguously storing the measurement data together with sample-specific data, e.g. a patient identification code, and the data processing unit of the data processing device co-operates with this storage of the connected handheld device. With this feature mixing-up of samples and patients can be avoided, since the encoding of the measurement data with the patients identification code takes place at the point of care, e.g. at the patients bed. Also other sample-specific data or information can be stored with the measurement data, e.g. an operator identification code, date and time of taking the sample. In this embodiment, the handheld device therefore provides an assignment of patient and/or operator identity to each measuring data.

Another improvement can be achieved, when the handheld device is provided for storing the measurement data and sample-specific data of at least two cartridges. The operator therefore can take and analyze several samples before transmitting the measurement data to the data processing device. This procedure saves time and therefore costs. The handheld device may also be used for taking measurements not only of one but also of different patients. When the handheld device will then be coupled to a respective one of the data processing devices, a transmission of the measured data from the handheld device to that data processing device e.g. will only be executed when the patient identifier provided by the data processing device matches with the patient identifier assigned to the respective measuring data. This allows that only such data will be exchanged, which relates to the same patient or to a defined patient group so that an unwanted date exchange can be avoided not only for avoiding mixing up different data, but also for data security reasons. In an example, a bedside monitor may handle only data of that particular bed, and therefore the data processing device will communicate data from the handheld device, where the patient of that bed has a clearly identity code. On the other hand a central station or a data base system can enable the data processing device to communicate data from the handheld device which are from a defined patient group and which are clearly identity coded.

According to a preferred embodiment the coupling between the handheld device and the data processing device is preferably only provided as long as the handheld device is in close (physical) proximity to the respective data processing device. This allows avoiding cross talk between different handheld devices and data processing units and/or unwanted data exchange between handheld devices and data processing devices that are not intended to communicate with each other. Furthermore, interference and disturbances can thus be reduced.

The data communication between the handheld device and the data processing device can be provided by any means as known in the art, such as wired or wireless communication. Wireless communication, in particular, can be any kind of electromagnetic communication, such as radio transmission, electromagnetic transmission in the low and high frequency range, and optical transmission in the visible, as well as invisible range. Alternatively, acoustic waves (ultrasound) or corresponding systems can be applied accordingly. State of the art modulation, demodulation and decoding techniques are described elsewhere. For a save communication between the handheld device and the data processing device it is advisable to use encoding and decoding techniques, in particular for wireless communication, and modulation techniques, in particular for communication via the wires used for power supply.

In case of wired data transmission, the assignment between the respected handheld device and the data processing device is unambiguous. However, in case of wireless data communication and when several different data communications are taking place, an unambiguous assignment between the respective handheld device and the data processing device should be ensured in order to provide a reliable data communication. This can be done by allowing data communication only when the handheld device is attached to the data-processing device (e.g. in a specific holding mechanism or insertion slot) or at least in close proximity. Alternatively, the handheld device and/or the data processing device might automatically assign a specific communication channel and/or coding scheme unique for each respective communication.

In a preferred embodiment, the diagnosis and/or analysis system comprises at least one adapter connectable to at least one peripheral device or application unit and to the data processing device. The adapter provides the data communication (wired or wireless in accordance as described above) between the handheld device and the peripheral device, thus providing an interface between the peripheral device and the handheld device. Therefore with help of this adapter the handheld device is connectable to peripheral devices via the data processing device. Examples for the peripheral devices can be printers, displays, keyboards, barcode readers, computing devices such as personal computers (PCs), patient monitors, central stations, data bases and information systems, or the like. The adapter provides means to adopt communication to the thereto coupled peripheral devices or application units.

It is suitable if the adapter communicates to the peripheral device in a bi-directional mode, so that the data processing device communicates data and results of the handheld device in a way, the peripheral device can handle those data. In a further embodiment the adapter enables the handheld device to being software updated by a peripheral device, which can be an internal or an external network. Not only the software can be updated such way, but also the calibration and quality check of the handheld device can thus be performed.

The data processing device may further comprise interfaces to other input and output units (like a printer, a display, a keyboard or a barcode scanner), and/or a power supply, batteries and/or charger to supply the handheld device. These improvements also include save and unambiguous data communication.

It is clear that the invention can be partly or entirely embodied by one or more suitable software programs, which can be stored on or otherwise provided by any kind of data carrier, and which might be executed in or by any suitable data-processing unit.

Other objects and many of the attendant advantages of the present invention will be readily appreciated and become better understood by reference to the following detailed description when considering in connection with the accompanied drawings. Features that are substantially or functionally equal or similar will be referred to with the same reference sign(s).

Figure 1:
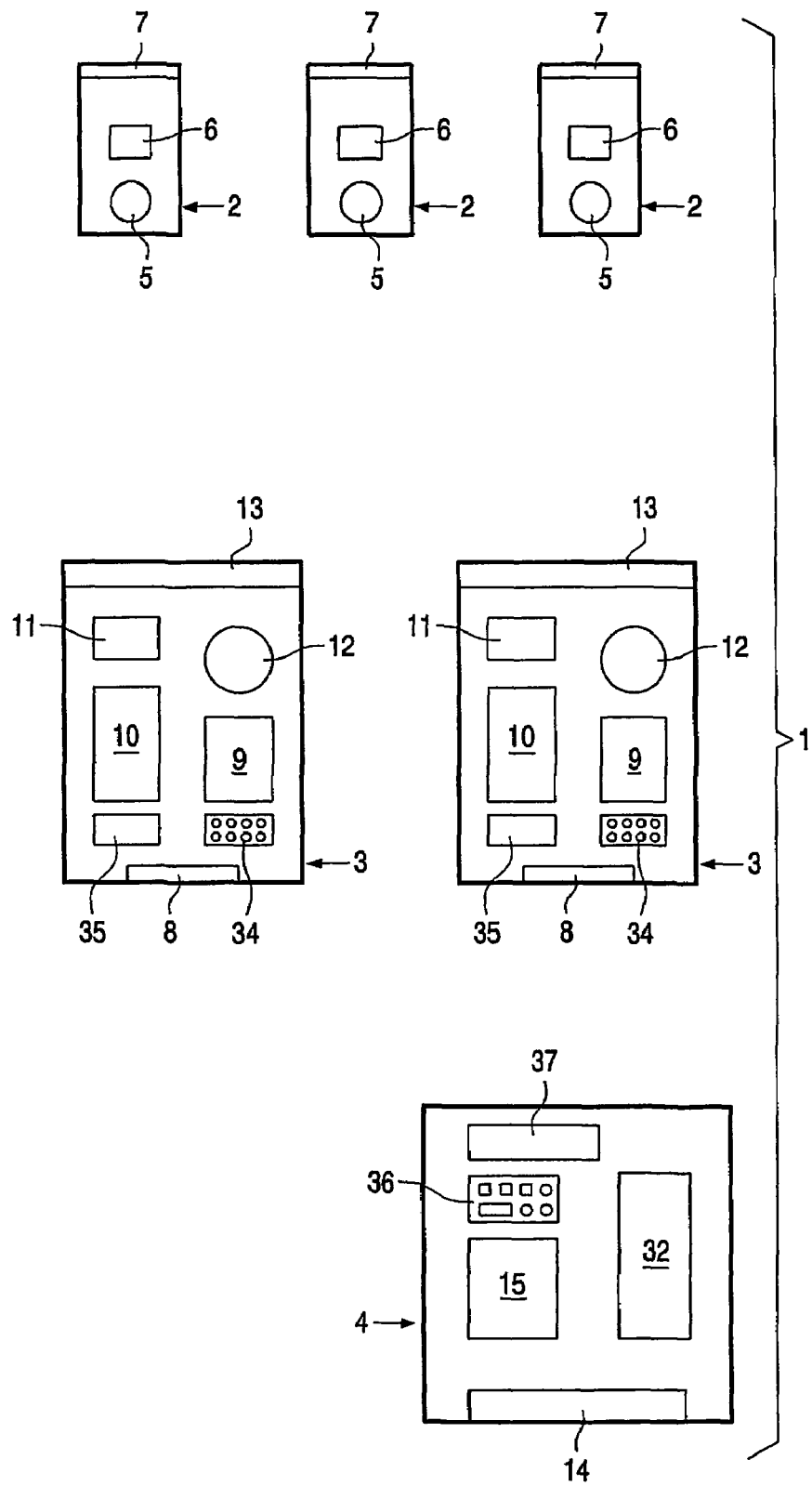
FIG. 1 shows a diagnosis and/or analysis system according to the invention.

According to FIG. 1 a system 1 for point of care diagnosis and/or analysis of a body fluid of a patient comprises at least one cartridge 2, at least one handheld diagnosis and/or analysis device 3 and at least one data processing device 4. The system 1 shown in FIG. 1 has e.g. three cartridges 2 and two handheld devices 3. It is clear, that any number of cartridges 2, handhelds 3 and processing devices 4 is possible.

Each cartridge 2 comprises a sample receiving room 5 for receiving a sample of the body fluid, in particular blood, to be diagnosed and/or analyzed. The cartridges 2 also comprise a diagnosis and/or analysis arrangement 6 for measuring at least one physiological parameter of the sample. This arrangement 6 can provide electrical or optical signals correlating with the physiological parameters, since the respective cartridge 2 is coupled with one of the respective handheld devices 3. To this aim each cartridge 2 has a first interface 7 and each handheld device 3 has a second interface 8 complementary to at least one of the first interfaces 7. Different types of cartridges 2 can have different first interfaces 7 and the respective handheld devices 3 therefore can have different types of second interfaces 8.

Each handheld device 3 comprises a measurement arrangement 9 co-operating with the diagnosis and/or analysis arrangement 6 of the cartridge 2 connected to the handheld 3 via the interfaces 7 and 8. This measurement arrangement 9 is provided for measuring the physiological parameter or the signals correlating therewith. The measurement arrangement 9 generates measurement data of the parameter or of the correlating signals, respectively. The handhelds 3 also comprise a processor 10, a memory 11 and a power supply 12. The processor 10 controls the measurement procedure and the storing of data in the memory 11. The power supply 12 e.g. is a battery, in particular a rechargeable battery. Such a handheld 3 may also have an input unit 34 like a keypad coupled with the processor 10. Such a handheld 3 may also be provided with an output unit 35 like a display.

According to the invention each handheld device 3 comprises a third interface 13 for coupling the respective handheld 3 to the data processing device 4, which to this aim has a complementary fourth interface 14. The data processing device 4 also has a data processing unit 15 co-operating with the processor 10, when the respective handheld 3 is coupled to the data processing device 4 via the interfaces 13 and 14. The data processing unit 15 can read the measurement data out of the memory 11 and performs further processing of this measurement data. Also the data processing device 4 may be provided with an input unit 36 like a keyboard and/or an output unit 37 like a display or a monitor. Since the handheld device 3 is coupled with the data processing device 4 the input unit 34 of the handheld device 3 can be used for data input into the data processing device 4 and/or for controlling the data processing device 4, and/or the output unit 35 of the handheld device 3 can be used for data output of the data processing device 4. Vice versa, the input unit 36 of the data processing device 4 can be used for data input into the handheld device 3 and/or for controlling the handheld device 3, and/or the output unit 37 of the data processing device 4 can be used for data output of the handheld device 3.

As depicted in FIG. 1 the data processing device 4 is provided with a power supply 32 for charging the battery 12 of the handheld device 3. The charging or recharging of the battery 12 automatically tales place via the interfaces 13 and 14, since the handheld device 3 is connected to the data processing device 4.

Figure 2:
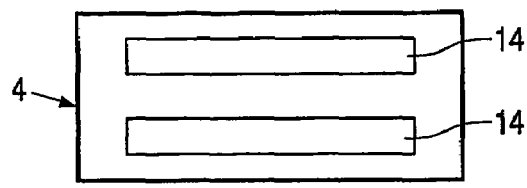
FIG. 2 shows a preferred embodiment of a data processing device according to the invention.

According to FIG. 2 a preferred embodiment of the data processing device 4 comprises at least two fourth interfaces 14, which may be provided for different types of handheld devices 3 having the complementary third interfaces 13. This data processing device 4 allows a simultaneous operation with several handheld devices 3.

Figure 3:
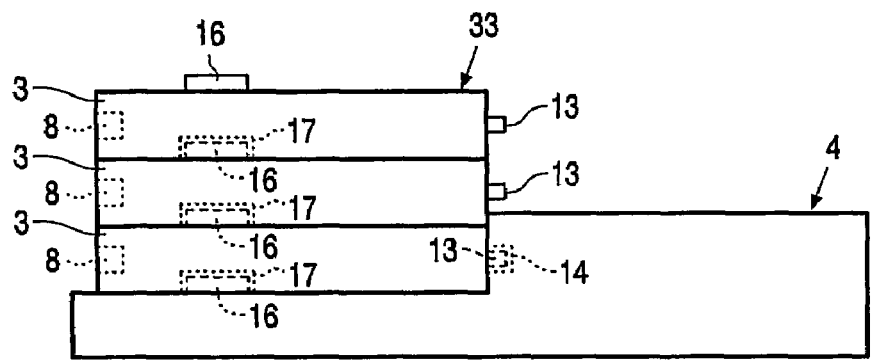
FIG. 3 shows another embodiment of a data processing device with several handheld devices.

In FIG. 3 the handheld devices 3 have additional complementary interfaces 16 and 17 provided for coupling two or more handhelds 3 together to form a stack 33 of coupled handhelds 3. All coupled handhelds 3 communicate via the third interface 13 of one of the handhelds 3 with the data processing device 4. In this case the three handhelds 3 of FIG. 3 communicate with the data processing device 4 via the third interface 13 of the lowest handheld 3. For a better communication the data transfer has to be coordinated. To this aim the handheld devices 3 are suitably configured in such a way, that they automatically provide a master-slave-configuration, if they are coupled together. In a preferred embodiment this master-slave-configuration allows its slave-members to perform the measurement of the plugged-in cartridge 2, while other operating units, in particular input and/or output units, are deactivated. In contrast thereto the operator units of the master-member co-operate with all members of the stack 33. Therefore the input and output units, in particular the keypad and the display, of the master-member provide a "human interface" for controlling all handheld devices 3 of the stack 33. Suitably the handheld device 3 on top of the stack 33 automatically forms the master-member of the master-slave-configuration.

For security reasons the measurement data of all handheld devices 3 may form an indivisible data set, which may be stored in the memory 11 of the master-member. If the stack 33 is coupled with the data processing device 4 this data set remains at the stack 33, since there is no explicit command, in particular of the operator, for copying or download the data set.

Figure 4:
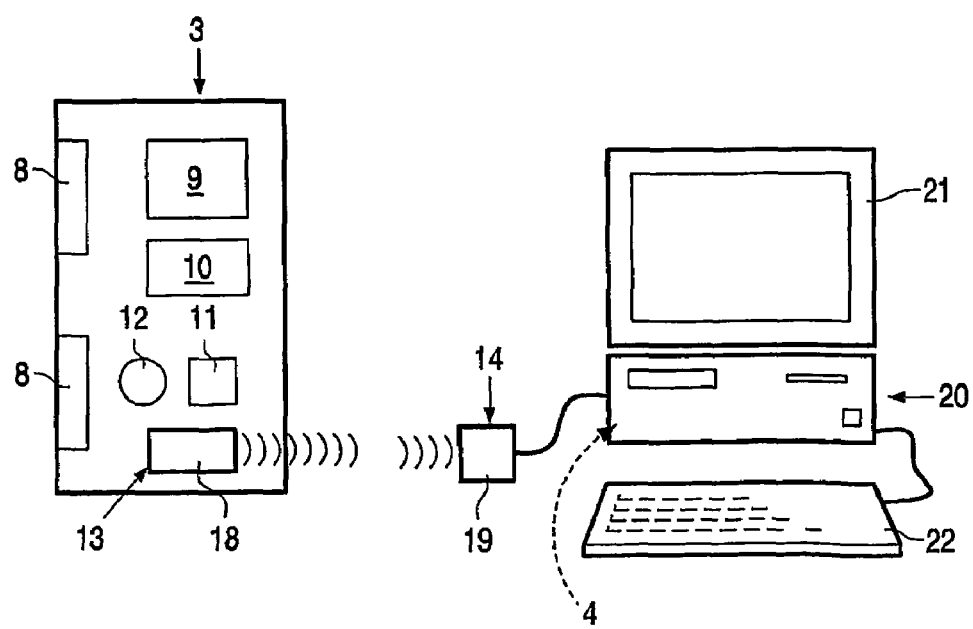
FIG. 4 shows a further embodiment of the data processing device and the handheld device.

According to FIG. 4 the third interface 13 and the fourth interface 14 are provided for a wireless data transfer. Therefore the third interface 13 comprises a first transmitter-receiver-unit 18 co-operating, e.g. via electromagnetic waves, with a second transmitter-receiver-unit 19 of the fourth interface 14.

The handheld device 3 of FIG. 4 shows two second interfaces 8 compatible for two different types of first interfaces 7 of different cartridges 2. According to the embodiment of FIG. 4 the data processing device 4 is incorporated into a personal computer (PC) 20, i.e. the data processing device 4 is partly or entirely embodied by one or more suitable software programs executed in the PC 20. The PC 20 e.g. comprises a monitor 21 and a keyboard 22.

Figure 5:
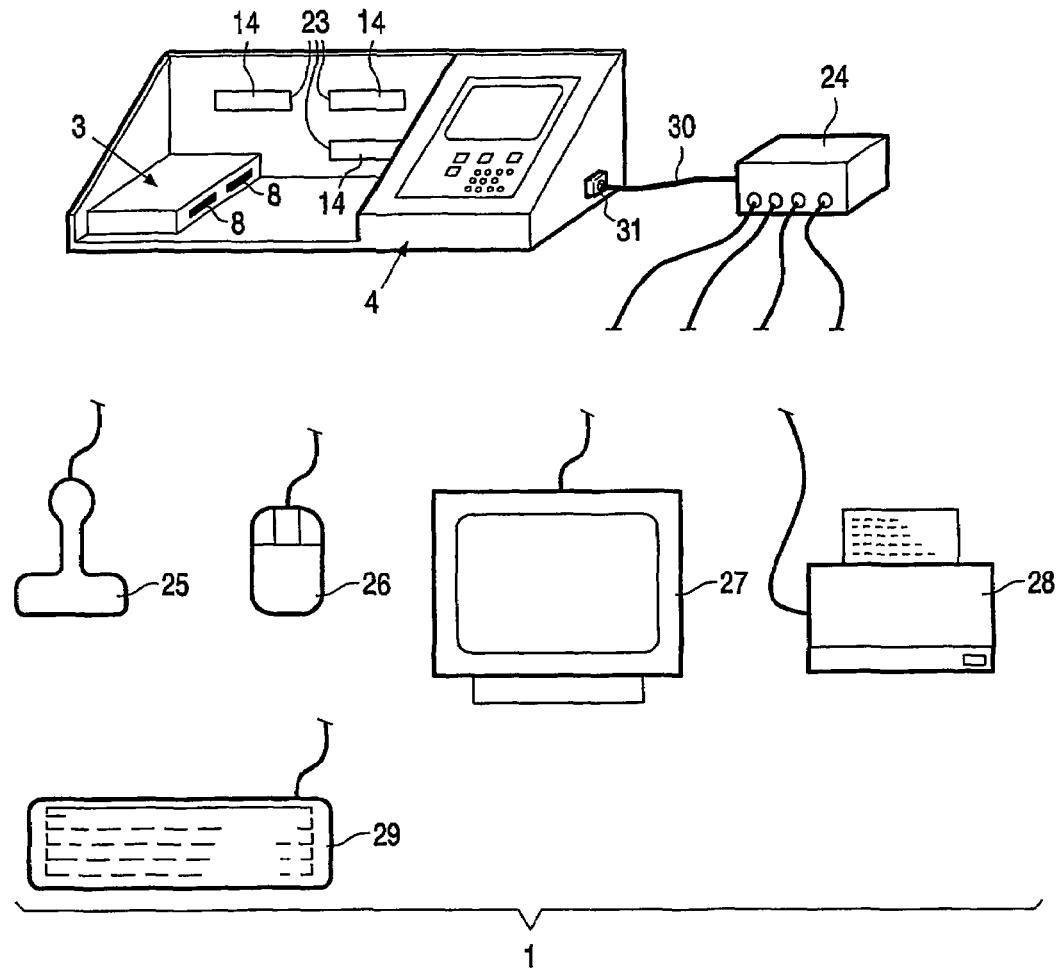
FIG. 5 shows another embodiment of the system according to the invention.

FIG. 5 depicts another embodiment of the system 1 according to the invention. The data processing device 4 has four insertion slots 23 each provided for receiving a single handheld device 3. Each insertion slot 23 comprises one of the fourth interfaces 14. In the example one of the handheld devices 3 is inserted into one of the insertion slots 23. This specific handheld 3 shows two second interfaces 8 provided for coupling two cartridges 2, in particular of different types, to the handheld 3. The system 1 of FIG. 5 comprises an adapter 24 and several different peripheral devices 25, 26, 27, 28 and 29. This adapter 24 is connected to the data processing device 4 by a wire 30 and suitable interfaces 31. It is also possible to incorporate this adapter 24 into the data processing device 4.

The adapter 24 is connectable to several peripheral devices 25 to 29, which e.g. may be a bar code reader 25, a computer mouse 26, a monitor 27, a printer 28 and a keyboard 29. Via the adapter 24 the data processing device 4 and the handheld device 3 can communicate with the coupled peripheral devices 25 to 29.

With help of the system 1 according to the invention an operator can take a body fluid sample, e.g. a blood sample, and insert it at the point of care, i.e. in the proximity of the patient, into the sample receiving room 5 of the suitable cartridge 2. Since this cartridge 2 is coupled to one of the handheld devices 3 the physiological parameters of the sample can be measured at the point of care. The generated measuring data is stored in the memory 11 and if the handheld 3 is coupled to one of the data processing devices 4 the measurement data can be processed by the processing unit 15.

In a preferred embodiment the handheld device 3 is provided for storing the measurement data of at least two samples or two cartridges 2, respectively. To avoid mixing up data the handheld device 3 is provided for encoding the measurement data with sample specific data or information. Preferably the handheld device 3 uses a patient identification code for encoding the measurement data. Other important sample specific data used for encoding with the measurement data could be an operator identifying code and the date and time of taking the sample. The sample specific data could e.g. be provided by input via a keyboard or keypad.

Since the handheld device 3 is provided for storing more than one measurement data the diagnosis and/or analysis procedure at point of care can be improved.

LIST OF REFERENCES 1. diagnosis and/or analysis system
2. cartridge
3. handheld diagnosis and/or analysis device
4. data processing device
5. sample receiving room
6. diagnosing and/or analyzing arrangement
7. first interface
8. second interface
9. measurement arrangement
10. processor
11. memory
12. power supply/battery
13. third interface
14. fourth interface
15. data processing unit
16. additional interface
17. additional interface
18. first transmitter-receiver-unit
19. second transmitter-receiver-unit
20. personal computer
21. monitor
22. keyboard
23. insertion slot
24. adapter
25. peripheral device/bar code reader 26. peripheral device/computer mouse
27. peripheral device/monitor
28. peripheral device/printer
29. peripheral device/keyboard
30. wire
31. interface
32. power supply
33. stack of handhelds 3
34. input unit of 3
35. output unit of 3
36. input unit of 4
37. output unit of 4

The invention claimed is:

1. System for point of care diagnosis and/or analysis of a body fluid of a patient, comprising:
   at least one cartridge, having:
      a sample receiving room for receiving a sample of the body fluid to be diagnosed and/or analyzed,
      a diagnosing and/or analyzing arrangement for measuring at least one physiological parameter of the sample,
      a first interface for connecting the cartridge to at least one handheld diagnosis and/or analysis device, the at least one handheld diagnosis and/or analysis device, having:
         at least one second interface for connecting one of said cartridges to the handheld device,
         a measurement arrangement co-operating with the connected cartridge for measuring the physiological parameter and generating measurement data thereof,
         at least one third interface for connecting the handheld device to a data processing device, the data processing device, having:
            at least one fourth interface for connecting one of said handheld devices to the data processing device,
            a data processing unit co-operating with the connected handheld device for further processing the measurement data; and wherein
   at least one of said handheld devices comprises a memory for unambiguously storing the measurement data together with sample-specific data, and
   the data processing unit of the at least one of said data processing device co-operates with the memory of the connected handheld device.

2. System according to claim 1, wherein
   at least one of said handheld devices comprises a rechargeable battery, and, wherein
   the data processing device comprises a power supply for charging the battery of the handheld device, when the handheld device is connected to the data processing device.

3. System according to claim 2, wherein the power supply of the data processing device is provided for charging the battery of the handheld device via the coupled third interface and fourth interface.

4. System according to claim 1, wherein the handheld device and the data processing device are configured in such a way, that they automatically or manually by user request create a master-slave-configuration.

5. System according to claim 4, wherein:
   the data processing device comprises a data input unit and/or a data output unit,
   the handheld device comprises a data input unit and/or a data output unit, such that when the handheld device and the data processing device are coupled together the data input units of one of the measuring device and the handheld device are connected and the data output units are automatically or manually by user request transferred to the master-member of the master-slave-configuration.

6. System according to claim 1, wherein the sample-specific data is at least a patient identification code and/or an operator identification code and/or time and date of the sample.

7. System according to claim 1, wherein at least one of said handheld devices is provided for storing the measurement data and sample-specific data of at least two cartridges.

8. System according to claim 1, wherein at least one of said handheld devices has at least two second interfaces for connecting two different types of said cartridges.

9. System according to claim 1, wherein
   the first interface and the complementary second interface, and/or
   the third interface and the complementary fourth interface are provided for wired and/or wireless data transfer.

10. System according to claim 1, wherein at least one of the handheld devices has an ergonomic casing.

11. System according to claim 1, wherein the data processing device and the handheld device are configured in such a way, that a wireless data transfer is only provided as long as the handheld device is in a predetermined close proximity to the respective data processing device.

12. System according to claim 1, wherein
   the system comprises at least one adapter, wherein
   the data processing device is connectable to the adapter, and wherein
   the adapter is connectable to at least one peripheral device.

13. System according to claim 1, wherein the data processing device is or comprises a personal computer and/or a database.

14. The system according to claim 1, wherein the diagnosing and/or analyzing arrangement is configured to provide electrical or optical signals correlating with the physiological parameter.

15. System for point of care diagnosis and/or analysis of a body fluid of a patient, comprising:
   at least one cartridge, having:
      a sample receiving room for receiving a sample of the body fluid to be diagnosed and/or analyzed,
      a diagnosing and/or analyzing arrangement for measuring at least one physiological parameter of the sample,
      a first interface for connecting the cartridge to each of or at least two handheld diagnosis and/or analysis devices,
   each of the at least two handheld diagnosis and/or analysis devices, having:
      at least one second interface for connecting one of said cartridges to each handheld device,
      a measurement arrangement co-operating with the connected cartridge for measuring the physiological parameter and generating measurement data thereof,
      at least one third interface for connecting each handheld device to a data processing device,
   the data processing device, having:
      at least one fourth interface for connecting one of said at least two handheld devices to the data processing device,
      a data processing unit co-operating with the connected handheld device for further processing the measurement data; and wherein
   at least one of said handheld devices comprises a memory for unambiguously storing the measurement data together with sample-specific data, and the data processing unit of the data processing device co-operates with this memory of the connected handheld device, and wherein each of the at least two handheld devices are provided with complementary interfaces for coupling the handheld devices together, wherein the coupled handhold devices are configured for connection to the data processing device via the third interface of one of the coupled handhold devices, wherein all coupled handheld devices communicate via this one third interface with the data processing unit of the data processing device.

16. System according to claim 15, wherein each of the at least two handheld devices are configured in such a way, that the coupled handheld devices automatically create a master-slave-configuration.

17. System according to claim 16, wherein each of the at least two hand held devices include a data in input unit and a data output unit and the hand held devices are configured to be coupled in a stack such that data inputs and data outputs are transferred automatically or manually by user request to the data input unit and data output unit of the master hand held device.

18. The system according to claim 15, wherein the diagnosing and/or analyzing arrangement is configured to provide electrical or optical signals correlating with the physiological parameter.

19. Handheld device for use in connection with a system for point of care diagnosis and/or analysis of a body fluid of a patient comprising:

at least one second interface for connecting a first interface of a cartridge having a sample receiving room for receiving a sample of a body fluid to be diagnosed and/or analyzed to the handheld device, a measurement arrangement co-operating with the connected cartridge for measuring the parameter and generating measurement data thereof, at least one third interface for connecting the handheld device to a data processing device of the system;

a memory for unambiguously storing the measurement data together with sample-specific data, and the data processing unit of the data processing device co-operates with this memory of the connected handheld device.

* * * * *